United States Patent [19]
Peterson et al.

[11] Patent Number: 5,883,084
[45] Date of Patent: Mar. 16, 1999

[54] TREATMENT OF RESPIRATORY DISEASES UTILIZING α-TOCOPHERYL-PHOSPHOCHOLINE

[75] Inventors: Andrew C. Peterson; Thaddeus P. Pruss, both of Madison, Wis.

[73] Assignee: Clarion Pharmaceuticals Inc., Madison, Wis.

[21] Appl. No.: 93,128

[22] Filed: Jun. 8, 1998

[51] Int. Cl.[6] .................. A61K 31/685; A61K 31/355
[52] U.S. Cl. ............................... 514/78; 514/458
[58] Field of Search ........................ 514/78, 458

[56] References Cited

U.S. PATENT DOCUMENTS

| | | |
|---|---|---|
| 4,312,860 | 1/1982 | Clements . |
| 4,751,334 | 6/1988 | Turner et al. . |
| 5,110,806 | 5/1992 | Clements . |
| 5,299,566 | 4/1994 | Davis et al. . |
| 5,614,216 | 3/1997 | Janoff . |
| 5,763,423 | 6/1998 | Yazdi et al. ........................ 514/78 |

OTHER PUBLICATIONS

Braga et al., Drugs in Bronchial Mucology, Raven Press, New York 1989.

Cohen et al., Total Synthesis of All Eight Stereoisomers of α–Tocopheryl Acetate. Determination of Their Diastereoisomeric and Enantiomeric Purity by Gas Chromatography, *Helv. Chimica Acta.* (1981), 64:1158–1173.

Chan et al., Synthesis of (2R,4'R,8'''R)–α–Tocopheryl Acetate (Vitamin E. Acetate) Using [3,3] Sigmatropic Rearrangement, *J. Org. Chem.* (1978), 43:3435–3440.

Chand et al., *Agents and Actions* (1993), 38:165–170.

Creuwals et al., *Lung* (1997), 175:1–39.

Kiyose et al., *Lipids* (1995), 30(11):1015–1018.

Puchelle et al., *Eur. J. Clin. Invest.* (1985), 15:389–394.

Rana et al., *Biochemistry* (1993), 32:27–31.

Revak et al., *Am. Rev. Respir. Dir.* (1986), 134:1258–1265.

Robeson et al., Isolation of an 1–Epimer of Natural d–α–Tocopherol, *J. Am. Chem. Soc.* (1962), 84:3196–3197.

M.A. Trush et al., "The Generation of Chemiluminescence by Phagocytic Cells," *Methods of Enzymology* (1978), 57:462–494.

*Primary Examiner*—Raymond Henley, III
*Attorney, Agent, or Firm*—DeWitt Ross & Stevens S.C.; Salvatore R. Conte, Esq.

[57] ABSTRACT

Disclosed is a method of treating respiratory diseases comprising treating the lungs with an therapeutically-effective amount of α-tocopheryl-phosphocholine or a pharmaceutically-acceptable salt thereof, wherein the amount is administered is effective to make breathing easier.

12 Claims, No Drawings

TREATMENT OF RESPIRATORY DISEASES UTILIZING α-TOCOPHERYL-PHOSPHOCHOLINE

FIELD OF THE INVENTION

The invention is directed to the use of α-tocopherylphosphocholine to treat respiratory diseases. The invention specifically includes the use of α-tocopherylphosphocholine to treat inflammation of the respiratory system, as a pulmonary surfactant, and as a mucolytic agent to thin or lower the viscosity of tenacious mucus.

DESCRIPTION OF THE PRIOR ART

The phosphocholine ester of α-tocopherol, α-tocopherylphosphocholine (also known as α-tocopherol-phosphocholine), a method of manufacturing same, and pharmaceutically-acceptable salts thereof have been described in Japanese Public Patent Disclosure No. 1-2111578, published Aug. 24, 1989.

Diseases of the respiratory system feature lowered pulmonary surfactant performance and inflammation which gives rise to impaired clearance of mucus. As used herein, the term "respiratory disease(s)" encompasses diseases involving the parenchyma (alveoli), such as adult respiratory distress syndrome (ARDS), respiratory distress syndrome (RDS), emphysema, pneumonia and pulmonary fibrosis, and diseases involving the conducting airways, such as asthma, bronchitis, chronic obstructive pulmonary disease and cystic fibrosis, among others.

The lung is an organ comprising 6% of the mammalian body volume. The primary purpose of the lung is to facilitate gas interchange and as a consequence has a large surface area which is constantly in contact with a hostile environment. Lung surfactant is a material ordinarily secreted onto the surface of lung alveoli to facilitate gas exchange. The natural surfactant coats the surface of the alveoli and provides the proper mechanical stability by reducing the surface tension at the air-alveolar interface {L. A.J. M. Creuwels et al., *Lung* (1997) 175:1–39}.

It is generally recognized that a deficiency in lung surfactant is the cause of RDS in premature babies and infants. Although such deficiency is not the primary factor in the development of ARDS, it may contribute significantly to the pathophysiology of the disorder.

RDS is the leading cause of death and disability among premature infants. In addition, about 150,000 cases of ARDS are reported annually with 60–80% mortality. To treat RDS and ARDS, a number of natural surfactants (human and bovine) and synthetic surfactants have been administered to the lungs of human subjects, for example, by inhalation of an aerosol formulation.

A complex array of compounds comprise natural mamallian pulmonary surfactant; the approximate composition is 90 wt. % lipids, 8 wt. % proteins and 2 wt. % carbohydrates. Adult bovine lung surfactant extract, which is obtained from adult bovine lung lavage, has been shown to contain 84% phosphatidyl cholines {F.R. Rana et al., *Biochemistry* (1993) 32: 27–31}. Dipalmitoyl phosphatidylcholine (DPPC) is the major component (about 80%) of natural human lung surfactant.

In general, most synthetic inhalant surfactant formulations contain DPPC, since it is known that DPPC can improve respiratory function in patients with RDS and ARDS. It does so by decreasing the surface tension of the alveoli of the lung thereby permitting them to open more readily to exchange oxygen and carbon dioxide. For example, see U.S. Pat. No. 5,299,566, which discloses a method for preparing a surfactant dispersion containing DPPC; U.S. Pat. No. 5,110,806, which discloses a synthetic surfactant containing DPPC, a long chain alcohol and a nonionic surfactant; U.S. Pat. No. 4,571,334, which discloses various drugs in combination with lung surfactant; U.S. Pat. No. 4,312,860, which discloses a synthetic surfactant containing DPPC and a fatty alcohol; and U.S. Pat. No. 5,614,216 which discloses a synthetic surfactant composition containing a mixture of phosphatidylcholine, phosphatidylethanolamine and cholesterol.

Disorders of the upper airways involve altered secretion of lung surfactant and/or alteration in the composition of the mucus. Asthma, chronic bronchitis and cystic fibrosis, in particular, are associated with hypersecretion of lung surfactant. Alterations in mucous composition usually accompany this hypersecretion and lead to increases in the viscosity of the mucus. As a consequence, patients suffering from these airways disorders experience a progressive difficulty in clearing mucus from their lungs. The patient experiences airway obstruction, oftentimes severe, and will essentially drown in mucus secretions if left untreated.

There are several reported drugs which have been shown to have a beneficial effect on airway clearance of mucus, for example, through their effect on cilia or by altering the physical properties of mucous secretions. One class of such compounds are based on iodide compounds. Treating the lungs with a saturated solution of potassium iodide or iodinated glycerol, is thought to stimulate the secretion of "thinner" secretions that are easier to clear. Another class is represented by N-acetyl cysteine. The viscosity of pulmonary mucous secretions depends largely on the concentration of mucoprotein in the mucus. The free sulfhydryl groups in N-acetyl cysteine are thought to open mucoprotein disulfide bonds, thereby reducing the viscosity of mucus. For a review of mucolytic drugs, see P. C. Braga: *Drugs in Bronchial Mucology*, Raven Press, New York, 1989.

Inflammation is a pervasive symptom which accompanies respiratory diseases and occurs in response to local trauma, bacterial infection, viral infection, allergic and immunogenic reactions, and the like. Inflammatory cells in the airways release mediators which can trigger or block the secretion of components of lung surfactant. Infection of the airways in cystic fibrosis, for instance, is associated with abnormal Theological and transport properties of airway secretions which may be responsible for the severity of the disease {E. Puchelle et al., *Eur. J. Clin. Invest.* (1985) 15:389–394}.

Pulmonary fibrosis is a pathological condition caused by viral pneumonias, drug reactions, chemical vapors and dusts. In addition, the early stages of pulmonary fibrosis are marked by the appearance of fluid and cellular debris in the alveoli. This exudate promotes an inflammatory reaction characterized by interstitial edema and invasion by leukocytes, macrophages, neutrophils, fibroblasts and eosinophils. These inflammatory cells also produce reactive oxygen species. Destruction of the alveoli occurs progressively as the reactive oxygen species and inflammation continues.

Over time, the growth of fibrous tissue at the expense of other tissues prevails. As the fibrosis proceeds, fibrotic thickening of the alveoli results. The lungs become stiff and shrunken with the formation of small microcysts in the parenchema and base of the lung. Patients exhibit difficulty in breathing, and coughing is unproductive. The later stages of pulmonary fibrosis are generally termed diffuse interstitial pulmonary fibrosis and is usually fatal. As a result of the destruction of type-II pneumocytes (alveolar lung surfactant producing cells) the production and integrity of the lung surfactant is compromised in pulmonary fibrosis.

Applicant is unaware of any references reporting that α-tocopheryl-phosphocholine has one or more utilities as a pulmonary surfactant, mucolytic, and/or anti-inflammatory.

SUMMARY OF THE INVENTION

The invention is directed to a method of treating a respiratory disease in a mammal afflicted with the same. The method comprises administering to the mammal a therapeutically-effective amount of α-tocopheryl-phosphocholine or a pharmaceutically-acceptable salt thereof, the amount being effective to make respiration easier. More specifically, the method is drawn to treating, without limitation, various respiratory diseases including asthma, bronchitis, chronic obstructive pulmonary disease, cystic fibrosis, emphysema, pneumonia, pulmonary fibrosis, respiratory distress syndrome (RDS), adult respiratory distress syndrome (ARDS), and combinations thereof.

The invention is further directed to a method of improving the clearance of mucus from the lungs in a mammal afflicted with a pulmonary disorder involving thickened or accumulated pulmonary mucous secretions. Here, the method comprises delivering to the lung airways of the mammal an effective mucus-clearing or mucolytic amount of α-tocopheryl-phosphocholine or a pharmaceutically-acceptable salt thereof. The terms "mucus-clearing" and "mucolytic" are used synonymously herein and refer to the ability of the subject compounds to decrease the viscosity of tenacious mucus and to increase the mobility of mucus across the surface of underlying pulmonary tissues.

The invention is further drawn to a method of improving bronchial mucus transport in a mammal in need thereof. The method comprises administering to the lung airways of the mammal a therapeutically-effective mucus transport-increasing amount of α-tocopheryl-phosphocholine or a pharmaceutically-acceptable salt thereof.

It is preferred that the α-tocopheryl-phosphocholine is delivered to the lung airways of the subject being treated in the form of an aerosolized liquid, an aerosolized powder, or a micronized dry powder.

It has now been found that α-tocopheryl-phosphocholine, also referred to herein as CPR 2001, and its pharmaceutically acceptable salts (collectively the "subject compounds") are useful therapeutic agents for preventing, inhibiting, treating, and otherwise ameliorating the symptoms of respiratory diseases in several aspects.

Specifically, the subject compounds are useful to treat the underlying features of asthma, bronchitis, chronic obstructive pulmonary disease, cystic fibrosis, emphysema, pneumonia, pulmonary fibrosis, RDS, ARDS, and other respiratory diseases. The subject compounds are also useful to supply lung surfactant to the damaged alveoli in patients suffering from various respiratory diseases. The subject compounds are also useful mucolytics which aid in clearing viscid mucus from the lungs.

It is a primary aim and object of the invention to provide a method of treating respiratory diseases with pharmaceutical compositions containing α-tocopheryl-phosphocholine.

Another aim of the invention is to provide a method to ease clearing pulmonary mucus from the lungs comprising administering α-tocopheryl-phosphocholine to the lungs or airways of a patient in need of such treatment.

A still further aim of the invention is to provide a method of reducing the viscosity of pulmonary mucus by administering α-tocopheryl-phosphocholine to the lungs or airways of a patient in need of such treatment.

It is a still further object of the present invention to provide a method of ameliorating a variety of pulmonary disorders involving airway obstruction due to accumulated mucous secretions by administering α-tocopheryl-phosphocholine to the airways or lungs of a patient suffering from such a disorder.

It is a still further of the present invention to provide a method of treating pulmonary inflammation by administering α-tocopheryl-phosphocholine to the airways or lungs of a patient suffering from pulmonary inflammation.

Humans are among the mammals that can be treated by the methods of the invention.

The inventive method comprises administering a therapeutically-effective amount of α-tocopheryl-phosphocholine which is represented by the general Formula I:

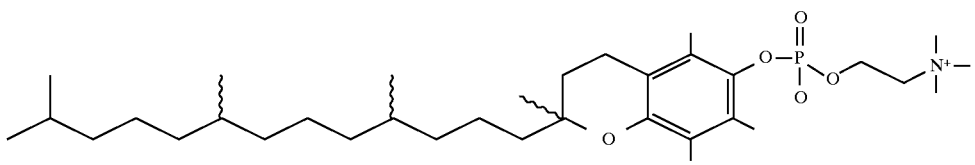

wherein the amount administered is effective to make breathing easier. Administration of the compounds is effective to lessen the viscosity and or increase the mobility of pulmonary mucus and effective to reduce pulmonary inflammation.

Those skilled in the art will immediately recognize that α-tocopheryl-phosphocholine has three asymmetric carbon atoms in its structure and therefore has 8 stereoisomers (4 pairs of enantiomers). The compound as used in accordance with the present invention may be one or a mixture of two or more of the biologically-active stereoisomers. Each of the stereoisomers is biologically active (see Kiyose et al (1995) Lipids 30(11):1015–1018). The invention encompasses use of all of the stereoisomers of the compound of Formula I, as well as the pharmaceutically-acceptable salts of the compounds (including the stereoisomers) of Formula I. Unless specifically qualified otherwise, reference herein to "compound(s) of Formula I" or to "α-tocopheryl-phosphocholine" means any of the stereoisomers, alone or in any combination.

A substantially pure stereoisomer of Formula I may be obtained using conventional and well-known resolution methodologies such as chromatography using chiral columns or using stereoisomerically-appropriate precursors in the synthesis of the Formula I compound of interest. It is noteworthy that α-tocopherol as it occurs in nature (commonly referred to as d-α-tocopherol is the substantially pure 2R, 4'R, 8'R-stereoisomer (i.e., the isomer having an R configuration at all of the asymmetric centers). Cohen et al., *Helv. Chim. Acta* (1981) 64: 1158–1173. Synthetic methods for preparing in substantially pure form each of the 8 stereoisomers of α-tocopherol are known. See, for example, Cohen et al., supra; Chan et al., *J. Org. Chem.* (1978) 43, 3435–3440.; Robeson et al., *J. Am. Chem. Soc.* (1962) 84: 3196–3197.

Preparation of α-tocopheryl-phosphocholine can be carried out by art-recognized procedures, beginning with α-tocopherol. See, for example, Japanese Public Patent Disclosure No. 1-211578, published Aug. 24, 1989.

The compounds of Formula I, as a substantially equimolar mixture of the 8 stereoisomers, can be prepared from commercially available, synthetic α-tocopherol. (Known as "d,1-α-tocopherol," synthetic α-tocopherol is a substantially equimolar mixture of the 8 stereoisomers of α-tocopherol.)

The salts of α-tocopheryl-phosphocholine, the therapeutic use of which is within the scope of the invention, are pharmaceutically-acceptable salts and include acid addition salts, such as those made with hydrochloric, hydrobromic, hydroiodic, nitric, sulfuric, phosphoric, carbonic, acetic, citric or lactic acids, as well as salts made with bases, such as sodium hydroxide, potassium hydroxide or calcium hydroxide. The salts of the invention are made by conventional means well-known to those of ordinary skill in the art.

All isomers of the compounds of Formula I, including geometric and optical isomers, mixtures thereof, racemates thereof, and enantiomerically enriched or purified forms thereof, are encompassed within the term "compounds of Formula I."

DETAILED DESCRIPTION OF THE INVENTION

The invention is directed to a method of treating respiratory diseases by administering a therapeutically-effective amount of α-tocopheryl-phosphocholine to a mammal in need of such treatment. The amount is therapeutically effective in that it makes breathing easier in the recipient mammal.

The invention provides a method of alleviating respiratory distress due to tenacious pulmonary mucous secretions in a patient suffering from such distress. In the preferred embodiment, the method is accomplished by the intermittent inhalation of an aerosol or dry powder formulation of α-tocopheryl-phosphocholine to deliver an effective mucolytic amount of α-tocopheryl-phosphocholine to the lung airways. The mucolytic activity of the subject compounds are demonstrated in a standard animal model in the Examples provided below. The in vivo mucolytic assay is similar to that described by Chand et al. *Agents and Actions*, (1993) 38:165–170, incorporated herein by reference.

The invention also provides a method of administering a pulmonary surfactant to a patient in need thereof. As noted above, in the preferred embodiment, the method is accomplished by the intermittent inhalation of an aerosol or by directly pouring a liquid composition of α-tocopheryl-phosphocholine into the lungs of a patient in need of pulmonary surfactant, thereby delivering an effective surface-active amount of α-tocopheryl-phosphocholine.

The effectiveness of the subject compounds as surfactants is demonstrated in the Examples using a standard animal model of RDS, a disease which features a deficiency of pulmonary surfactant.

The invention also provides a method of alleviating respiratory distress due to pulmonary inflammation in a patient suffering from pulmonary inflammation. The method is accomplished, most preferably, by the intermittent inhalation of an aerosol or dry powder formulation of α-tocopheryl-phosphocholine to deliver an effective anti-inflammatory amount of α-tocopheryl-phosphocholine to the patient.

The anti-inflammatory activity of the subject compounds is demonstrated in the Examples using a standard in vitro assay which measures the inhibition of superoxide anion release from phorbol-12-myristate-13-acetate(PMA)-stimulated macrophages.

METHODS OF ADMINISTRATION

In mammalian subjects, α-tocopheryl-phosphocholine can be administered orally, parenterally, intravenously and, preferably by inhalation alone or in combination with an inert liquid or solid pharmaceutically-acceptable carrier. An appropriate carrier is selected based upon the method of administration chosen. Such pharmaceutical carriers are well-known in the art.

The in vivo dosage in humans and other mammals depends largely upon the affliction being treated, the time since onset of the condition, the progression of the disease, and the age and general health of the patient being treated. Determining the optimum dosage for any given patient is essentially an empirical and ongoing process. Inhibition of respiratory diseases in infants and children who are diagnosed early in the progression of the condition may optimally require a more (or less) aggressive treatment than in older patients in more terminal stages of a respiratory condition. Of primary importance in optimizing the most effective dosage is that each patient be carefully monitored throughout the course of treatment to follow the progression, if any, of the condition.

A suitable effective dose for most conditions ranges from about 1 mg/kg body weight to about 2 g/kg body weight per day, and is preferably in the range from about 10 to 500 mg/kg body weight per day (calculated as the non-salt form). The daily dose may be given as a single dose, multiple doses, e.g. two to six times per day. Dosages above or below the above-cited ranges are within the scope of the invention and such dosages may be administered to individual patients if the circumstances so dictate.

For example, in a 75 kg mammal, a typical daily dose might fall within the range of 100 mg to about 10 g per day. If discrete multiple doses are indicated, treatment might typically comprise four equal fractional doses given at 6 hour intervals to supply the total daily dosage.

The formulations may conveniently be presented in unit dosage form and may be prepared by any of the methods well-known in the art of pharmacy. The term "unit dosage" or "unit dose" is denoted to mean a predetermined amount of the active ingredient sufficient to be effective for treating each of the indicated disease states. All methods include the step of bringing the active compound into association with a carrier and one or more optional accessory ingredients. In general, the formulations are prepared by uniformly and intimately bringing the active compound into association with a liquid or solid carrier and then, if necessary, shaping the product into desired dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulations suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the compound of Formula I which upon dilution with an appropriate solvent give a solution suitable for parenteral administration.

Preparations for topical or local applications comprise aerosol sprays and dry powder inhalers and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the compounds of Formula I are preferable utilized at a concentration of from about 0.1% to 5.0% by weight.

In addition to the aforementioned ingredients, the formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

Aerosolized delivery of drugs to the lung airways has been employed in clinical practice for many years. A variety of medicinal agents have been utilized in aerosol therapy including, for example, mucolytics such as N-acetylcysteine and synthetic surfactant formulations containing DPPC and DSPC for treating patients with RDS and ARDS. The advantage of an aerosol delivery system is its wide-spread drug delivery to all lung regions intermittently over extended periods of time.

It is preferred that α-tocopheryl-phosphocholine be utilized as a dispersion in an aerosolized liquid formulations, ready for use. It is also much preferred that the formulation be suitable for use with art-recognized inhalation devices, such as a nebulizer or a metered-dose inhaler, without any further manipulation by the user. The subject compounds may also be prepared as a sterile lyophilized powder of appropriate average diameter for direct inhalation or, alternatively, the powder is first reconstituted with an aqueous carrier such as water or, preferably, a saline solution of about 0.4 to about 0.9 percent sodium chloride as a dispersion and delivered via an appropriate nebulizer or inhalant system. The recommended average diameter of the particulate dispersed powder along any axis is about 1 to 10 microns ($\mu$M) and, preferably, about 5 to 10 $\mu$M. In general, α-tocopheryl-phosphocholine is included in an amount from about 0.1 to 10 percent weight/volume dispersed in normal or slightly hypotonic saline with an art-recognized propellant, for example, dichlorodifluoromethane, presented as a metered-dose aerosol unit. Each actuation releases between 0.1 and 100 mg of α-tocopheryl-phosphocholine.

The technology for making aerosolized drug delivery systems is well documented. The compounds of Formula I are incorporated into such systems by art-recognized methodologies which need not be repeated in detail here.

It is also intended that α-tocopheryl-phosphocholine can be utilized in formulations which contain other ingredients suitable for inhalation therapy, for example, phospholipids, such as phosphatidylcholines, phosphatidylethanolamines, phosphatidylglycerols and the like. Furthermore, formulations which contain the subject compounds and tyloxapol, glycerol and/or fatty alcohols, such as hexadecanol, vitamin E, all-trans-retinol, cholesterol and the like are intended to be utilized when it is found to be desirable to do so.

In addition, formulations which comprise α-tocopheryl-phosphocholine and pulmonary surfactant proteins, such as pulmonary surfactant protein A (SP-A), pulmonary surfactant protein B (SP-B), pulmonary surfactant protein C (SP-C), pulmonary surfactant protein D (SP-D), and the like are intended to be utilized when it is found to be desirable to do so. It is further intended that formulations which comprise the subject compounds of Formula I and enzymes such as glutathione peroxidase and human deoxyribonuclease I, and the like are utilized when it is found to be desirable to do so. The compounds of Formula I may be used alone or in combination with other active ingredients suitable for aerosol delivery to the lung, for example, antibiotics, bronchodilators, mucolytics, 5-lipoxygenase inhibitors and the like.

In accordance with the present invention, the compounds of Formula I are efficacious in the treatment of respiratory diseases in which mucus viscosity or accumulated mucus and/or pulmonary inflammation is a major or contributing symptom. Such diseases include, without limitation, bronchitis, cystic fibrosis and asthma (see American Thoracic Society Symposia Excerpts, 1994 International Conference). The subject compounds are also efficacious in the treatment of chronic obstructive pulmonary disease, a disease also associated with increased pulmonary mucous secretion (see Ferguson and Chermiack (1993) Management of COPD, New Eng. J. Med., pp. 1017–1021). In addition, the subject compound are efficacious in treating respiratory diseases characterized by a deficiency of pulmonary surfactant. Such diseases include, without limitation, ARDS, RDS, emphysema, and pulmonary fibrosis.

EXAMPLES

The following Examples are included to illustrate the practice of the present invention. The Examples do not limit the scope of the present invention in any fashion.

Example 1
In Vitro Assay for Anti-Inflammatory Activity by Inhibition of Macrophage Activation Activation of alveolar macrophages is a critical component of pulmonary inflammation. In their activated state, alveolar macrophages secrete a variety of inflammatory mediators and reactive oxygen species. In the present in vitro model of inflammation, mouse macrophages are activated by phorbol-12-myristate-13-acetate (PMA). The intensity of macrophage activation in the presence or absence of the subject compounds is determined by measuring the respiratory burst (release of reactive oxygen species) of the macrophages.

The RAW 264.7 cell line (American Type Culture Collection, Rockville, Md., USA, Accession No. TIE 71) is a murine monocyte/macrophage line, the cells of which show many of the differentiative functions of a macrophage. Like macrophages, the cells are capable of phagocytosis and undergo an oxidative burst (increased oxygen consumption) and production of oxygen radicals (e.g., superoxide) in response to appropriate signals. Agents that inhibit the activation of these cells in vitro so as to inhibit the respiratory burst and corresponding production of oxygen radicals associated with activation interdict a critical step in the inflammatory process.

The respiratory burst and corresponding production of oxygen radicals that accompany macrophage activation can be measured in a variety of ways, including chemiluminescence based on the reaction of the oxygen radicals with luminol added to the culture medium (see M. A. Trush et al., 1978, "The Generation of Chemiluminescence by Phagocytic Cells.", Methods in Enzymology 57: 462–494). Chemiluminescence generated from luminol in the culture medium of macrophage cell lines is recognized in the art as a marker of macrophage activation. Materials:

Cell line: RAW 264.7 (ATCC TIB-71, attachment dependent);

Culture medium: Dulbecco's Modified Eagle's Medium (DMEM, Sigma Chemical Co. Cat. No. D-7777) with 10% Fetal Bovine Serum (FBS);

Standard protocol for culturing cell lines: in T-75 or T-150 flasks; 37° C.; 95% air, 5% $CO_2$; 100% humidity;

Cell line is passaged when approximately 80% confluent; with trypsin (1 mg/mL) and ethylenediamine tetraacetic acid (EDTA) (1 mM in Ca-Mg free Hank's balanced salt solution); at 1:4 to 1:5 split;

All procedures are performed aseptically in a Class II biological safety cabinet using standard Biosafety Level 2 (BL-2 containment procedures. In order to prevent genetic drift in stock cell lines, fresh cultures are prepared at approximately monthly intervals with cells thawed from liquid nitrogen storage. Methodology:

After cell passage, count cells with a hemocytometer; Adjust cell concentration to approximately 1,000,000 cells per mL;

Suspend cells in DMEM lacking phenol red and without FBS;

Pipette 1 mL of cell suspension into a standard luminometer cuvette (12×75 mm), commercially obtainable from Analytical Luminescence Laboratories, San Diego, Calif., USA;

Add luminol to final concentration of 0.2 mM;

Add test compound dissolved in phosphate buffered saline (PBS), or in dimethyl sulfoxide (DMSO) for final concentration levels ranging from 1 to 30 mM;

Add 100 nanograms of phorbol myristate acetate (PMA); and

Wait 1 minute and read photo counts (i.e., luminescence) on a Monolight 2010 luminometer available from Analytical Luminescence Laboratories, San Diego.

Data Analysis:

Calculate:
% Inhibition =

$$\frac{1 - L\{(\text{test compound}) - L(\text{background})\}}{L(\text{control}) - L(\text{background})} \times 100$$

| Concentration (mM) | α-Tocopherol (% Inhibition) | CPR 2001 (% Inhibition) |
|---|---|---|
| 30 | −14 | 56 |
| 10 | −6 | 31 |
| 3 | −6 | 13 |
| 1 | −3 | 5 |

Results:

With increasing concentration of CPR 2001, from 1 to 30 mM, anti-inflammatory activity markedly increases, in contrast to α-tocopherol. Thus, CPR 2001 has utility in respiratory diseases in which inflammation is a major or contributing factor, such as in bronchial asthma, pulmonary fibrosis, ARDS, emphasema, pneumonia, and cystic fibrosis. As shown by the above results, administration of CPR 2001 inhibits inflammation in an accepted in vitro model in a dose-dependent fashion.

Example 2

Mucolytic Activity in Mouse Tracheal Mucus

The procedure, which delivers the test compound to mice as an aerosol, is a modified assay for the evaluation of mucolytic activity in mice as described by Chand et al., previously cited.

1. The test animals are Hsd:1CR(CD-1) mice that weigh approximately 25 g each.

2. The test compound is diluted in normal saline to a concentration of 25 mg/mL and administered using a human De Vilbiss atomizer Model No. 15 at approximately 100 mg/kg. The control group receives saline. The nozzle is placed in the mouth of the mouse and 2 spray doses are given.

3. After 30 minutes, phenol red dissolved as a 5% solution in saline is given IP at a dose of 0.1 mL/10 g body weight.

4. Thirty minutes after phenol red administration, the animals are sacrificed by exposure to 100% $CO_2$.

5. The entire trachea is removed, the exterior blotted dry and the trachea washed in 1.0 mL saline. Thirty Minutes later, 0.1 mL of 1M NaOH is added to the tracheal washings to stabilize the pH of the lavage fluid.

6. The amount of phenol red secreted into the trachea is quantitated photometrically at 546 nm.

7. Calibration of the dose delivered is done by measuring the volume of five sprays per tube in five separate tubes. The average amount is 60.4 μL/spray with a range of 58–63 μL.

The test results indicate that the average measured percent change in mucolytic activity for α-tocopheryl-phosphocholine-treated mice is about 82.6% (5 mice), as compared to about 59.5% for N-acetylcysteine (5 mice) and zero percent for saline control (3 mice). Thus, the subject compound has utility in those diseases in which clearance of mucus is a major or contributing problem by acting as a mucolytic.

Example 3

Surfactant Activity in RDS Model Using Premature Fetal Rabbits

A common in vivo model for the evaluation of surfactants is lung compliance in premature fetal rabbits. This method is described in Revak et al., Am. Rev. Respir. Dir. (1986) 134:1258–1265. In this assay, the effectiveness of the subject compounds as lung surfactants is determined by evaluating dynamic lung compliance in premature fetal rabbits which are known to have difficulty initiating breathing due to low levels of natural lung surfactant.

1. The test animals are fetal rabbits delivered prematurely at 27 days of gestation.

2. The test solution is prepared by suspending the Formula I compound (120 g) in 6 mL of 10 mM HEPES buffer with sodium chloride (150 mM) at a pH of 7.4.

3. 0.2 mL of test solution is administered to the fetal rabbit before breathing commenced by endotracheal instillation and then monitored for breathing. The control group receives saline.

4. The fetal rabbit is ventilated and monitored for breathing.

5. After 30 minutes, the rabbit is examined for quality of breathing and color. A healthy pink color is indicative of good breathing. Lung volume and airway pressure are measured, and these results used to calculate dynamic compliance, expressed in arbitrary units as a ratio of flow to pressure per unit of body weight. The higher the value of measured compliance, the better the breathing of the test animal.

6. Compliance values are determined at 30 minute intervals for 90 minutes.

Animals treated with the subject compounds exhibited significantly greater compliance values, indicating that the subject compounds function as pulmonary surfactants. The positive results obtained in this Example illustrates the ability of α-tocopheryl-phosphocholine to serve as a pulmonary surfactant. The subject compounds therefore have utility in the treatment of those diseases which are characterized by a deficiency of natural pulmonary surfactant, such as RDS and ARDS.

Example 4
Histamine-Induced Airway Resistance:

The following is a protocol for the evaluation of antihistamine activity in anesthetized guinea pigs.

1. Guinea pigs of 650–1000 g are used to facilitate catheterization of the jugular vein and carotid artery. The guinea pigs are anesthetized with 35–45 mg/kg pentobarbital sodium. When or if the recordings are unstable, anesthetic additions are made during the course of the intervention. The cutdown is a ventral medial incision over the cervical area so that the trachea, jugular vein and carotid artery can be cannulated. The animals are immediately attached to a volume regulated Harvard® rodent respirator, Model 683, via a tracheostomy and the respirator is set at 60 respirations per minute and a volume of 8 ml/kg to maintain a normal arterial P-$CO_2$ of approximately 40 mmHg. Pancuronium, a muscle relaxant, is then given IV at a dose of 0.2 mg/kg to prevent spontaneous breathing. A tube is connected to the respirator pump and the endotracheal catheter is attached to a pressure transducing strain gauge and then to a 2-channel Gilson® physiological recorder. One channel of the recorder inscribes the pressure tracing from the airway; the second channel inscribes the pressure tracing from a similar strain gauge attached directly to a catheter inserted into the carotid artery. These two parameters are measured before and after each drug is given and at each increment in the dose response studies with each drug candidate and recorded. Total pulmonary resistance (TPR) is calculated as the difference between the expiratory pressure and inspiratory pressures with a constant volume.

After the anesthetic and muscle relaxant are given, the animal is allowed to stabilize. The airway is gently suctioned with a syringe, and the lungs are briefly inflated by closing the expiratory port on the ventilator until the pressure is approximately three times resting pressure. When the pressure returns to a steady state, this TPR is considered control pressure. The dose-related increases or decreases are quantitated against these controls to determine the percent inhibition of histamine activity. Two doses of histamine (1 mg/kg) are given as controls before the test compound is administered.

Results:

After induction with histamine, separate groups of animals were given salbutamol (10 μg/kg) or the same equivalent dosage of salbutamol encapsulated in liposomes of CPR 2001. After administering salbutamol alone, TPR briefly increased and then decreased below the control value. It took an average time of 1 hour 28 minutes for the TPR to return to the control value. When encapsulated in CPR 2001, the TPR also briefly increased above the control and then decreased below the control value. Here, however, it took an average time of 2 hours and 38 minutes for the TPR to return to the control value.

These results demonstrate that encapsulation into liposomes of CPR 2001 can extend the beneficial activity of medicinal compounds.

Example 5
Inhalation Cartridge

| Component | Amount per Cartridge |
| --- | --- |
| α-tocopheryl-phosphocholine | 5.0 mg |
| Lactose, q.s. | 25.0 mg |

The active ingredient, α-tocopheryl-phosphocholine, premicronized to a particle size between 10–50 microns in average diameter, is blended with normal tabletting grade lactose in a high energy mixer. The powder blend is micronized to a fine particle size between 1–10 microns and filled into appropriately sized hard gelatin capsules or cartridges on a suitable encapsulating machine. The respirable contents of the capsules or cartridges are administered using a conventional powder inhaler.

Example 6
Metered Liquid Dose

| Component | Amount per Cartridge |
| --- | --- |
| α-tocopheryl-phosphocholine | 5.0% by weight |
| isotonic saline | q.s. |

The active ingredient, α-tocopheryl-phosphocholine, is dissolved in a sufficient quantity of sterile isotonic saline to yield a solution which is 5% by weight Formula I compound. The solution is administered in the form or an aerosolized metered-dose via a suitable nebulizing device.

Example 7
Tablets

This is an illustrative example of tablets containing the subject compounds which may be prepared in conventional manner:

| Ingredients | Per Tablet (mg) |
| --- | --- |
| α-tocopheryl-phosphocholine | 50–100 |
| Lactose | 70 |
| Maize Starch | 70 |
| Polyvinylpyrrolidine | 5 |
| Magnesium Stearate | 5 |
| Tablet Weight | 200–250 |

Example 8

Capsules

Here is shown an example of capsules containing the subject compounds which may be prepared in conventional manner:

| Ingredients | Per Capsule (mg) |
| --- | --- |
| α-tocopheryl-phosphocholine | 50 |
| Lactose | 450 |
| Magnesium Stearate | 5 |
| Capsule Weight | 505 |

Example 9

Liquid for Parenteral or Intravenous Administration

What follows is an illustrative pharmaceutical composition for parenteral or intravenous administration of the subject compounds:

| Ingredients | Amount per ampoule |
| --- | --- |
| α-tocopheryl-phosphocholine | 50 mg |
| Buffering Agent | q.s. |
| Saline | 1 mL |

What is claimed is:

1. A method of treating a respiratory disease selected from the group consisting of bronchitis, chronic obstructive pulmonary disease, cystic fibrosis, emphysema, pneumonia, pulmonary fibrosis, respiratory distress syndrome, adult respiratory distress syndrome, and combinations thereof in a mammal afflicted with same comprising administering to the mammal a therapeutically-effective amount of α-tocopheryl-phosphocholine or a pharmaceutically-acceptable salt thereof.

2. The method of claim 1, which is a method to treat bronchitis.

3. The method of claim 1, which is a method to treat cystic fibrosis.

4. The method of claim 1, which is a method to treat chronic obstructive pulmonary disease.

5. The method of claim 1, which is a method to treat emphysema.

6. The method of claim 1, which is a method to treat pneumonia.

7. The method of claim 1, which is a method to treat pulmonary fibrosis.

8. The method of claim 1, which is a method to treat respiratory distress syndrome.

9. The method of claim 1, which is a method to treat adult respiratory distress syndrome.

10. A method of improving the clearance of mucus from the lungs in a mammal afflicted with a pulmonary disorder involving thickened or accumulated pulmonary mucous secretions, the method comprising delivering to the lung airways of the mammal an effective mucus-clearing amount of α-tocopheryl-phosphocholine or a pharmaceutically-acceptable salt thereof.

11. The method of claim 10, wherein the α-tocopheryl-phosphocholine is delivered to the lung airways in the form of an aerosolized liquid, an aerosolized powder, or a micronized dry powder.

12. The method of claim 10, wherein the amount administered is from about 1 mg/kg body weight to about 2 g/kg body weight per day.

* * * * *

UNITED STATES PATENT AND TRADEMARK OFFICE
CERTIFICATE OF CORRECTION

PATENT NO. : 5,883,084
DATED : March 16, 1999
INVENTOR(S) : Andrew C. Peterson and Thaddeus P. Pruss It is certified that error appears in the above-identified patent and that said Letters Patent is hereby corrected as shown below:

At column 2, line 47, please delete "Theological" and insert therefor -- "rheological"

At column 8, line 64, please delete "Accession No. TIE 71" and insert therefor -- "Accession No. TIB 71"

Signed and Sealed this

Twentieth Day of July, 1999

Attest:

Q. TODD DICKINSON

Attesting Officer

Acting Commissioner of Patents and Trademarks